United States Patent [19]
Rosoff et al.

[11] Patent Number: 5,503,983
[45] Date of Patent: Apr. 2, 1996

[54] METHOD OF DIAGNOSIS OF GIARDIASIS USING *GIARDIA LAMBLIA*-SPECIFIC STOOL ANTIGEN

[75] Inventors: John D. Rosoff, Mountain View, Calif.; Henry H. Stibbs, New Orleans, La.

[73] Assignee: Alexon Biomedical, Inc., Mountain View, Calif.

[21] Appl. No.: 66,628

[22] Filed: May 24, 1993

Related U.S. Application Data

[63] Continuation of Ser. No. 330,777, Mar. 30, 1989, abandoned.

[51] Int. Cl.⁶ .................. G01N 33/53; G01N 33/569; C07K 16/00
[52] U.S. Cl. .................. 435/7.22; 435/7.92; 435/7.94; 435/967; 530/389.5; 530/822
[58] Field of Search .................. 435/7.22, 7.92, 435/7.94, 967, 961; 530/389.5, 825

[56] References Cited

U.S. PATENT DOCUMENTS

| | | | |
|---|---|---|---|
| 4,118,469 | 10/1978 | Caldwell et al. | 424/1 |
| 4,530,908 | 7/1985 | Strand | 436/536 |

FOREIGN PATENT DOCUMENTS

| | | |
|---|---|---|
| 0138377 | 4/1985 | European Pat. Off. |
| 390460 | 10/1990 | European Pat. Off. |

OTHER PUBLICATIONS

Craft, et al., *J. Infect. Dis.*, 145:499–504 (1982).
Green, et al., *Lancet* ii:691–693 (1985).
Janoff, et al., *J. Clin. Microbiol.*, 27(3):431–435 (1989).
Nash, et al., *J. Clin. Micro.*, 25:1169–1172 (1987).
Rosoff, et al., *J. Clin. Micro.*, 23(5):905–910 (1986).
Rosoff et al., *J. Clin. Micro.*, 24(6):1079–1083 (1986).
Stibbs, et al., *J. Clin. Micro.*, 26(9):1665–1669 (1988).
Ungar, et al., *J. Infect. Dis.*, 149:90–97 (1984).
Vinayak, et al., *Pediatr. Infect. Dis.*, 4:383–386 (1985).
Alexander, et al., *Infect. Immunol.*, 15(1):313–321 (1977).
Crowle, et al., *Immunological Communications*, 1(4):325–336 (1972).
Norrild, et al., *Anal. Biochem.*, 81:432–441 (1977).
Rosoff, et al., *Alexon BiomedicalReprint Series*, 1(1):1–7 (1988).
Rosoff, *Alexon, Incorporated Clinical Parasitology*, pp. 2–13.

*Primary Examiner*—Toni R. Scheiner
*Assistant Examiner*—Patricia A. Duffy
*Attorney, Agent, or Firm*—Morrison & Foerster

[57] ABSTRACT

*Giardia lamblia*-specific antigen (GSA 65) and monospecific antibodies thereto are disclosed along with a method for the coprodiagnosis of giardiasis in mammals.

10 Claims, 6 Drawing Sheets

METHOD OF DIAGNOSIS OF GIARDIASIS USING *GIARDIA LAMBLIA*-SPECIFIC STOOL ANTIGEN

This application is a continuation of U.S. Ser. No. 07/330,777, filed Mar. 30, 1989, abandoned.

BACKGROUND OF THE INVENTION

This invention relates to highly purified *Giardia lamblia*-specific stool antigen (GSA 65) and polyclonal monospecific antibodies specific for it. This invention further relates to diagnosis of human infection caused by *Giardia lamblia*.

*Giardia lamblia* is a protozoan parasite which inhabits the small intestines of humans. It is the most common cause of defined waterborne diarrhea in the United States, and massive outbreaks of diarrhea, particularly in children, have occurred due to Giardia-contaminated water supplies and person to person transmission. This affliction is referred to as giardiasis.

Giardiasis affliction has been diagnosed traditionally by microscope detection of cysts or trophozoites in stools or in material retrieved from the small intestine by invasive methods. Diagnosis of infection with *Giardia lamblia* by microscopic examination of stool for ova and parasites (O&P) is a laborious process. Even after the various standard methods of stool preparation which increase the sensitivity of Giardia detection are carried out, the sensitivity of O&P microscopic examination is dependent upon a microscopist's skill in scanning each preparation. The diagnostic success rate of stool examination is roughly 50–70%. Moreover, infectious cysts may not always be excreted despite giardial infection, necessitating multiple stool examinations which may not result in positive diagnosis.

In recent years, efforts have been made to improve the sensitivity of giardial diagnosis methods. The focus of these efforts has been primarily on serologic testing for anti-giardial antibodies and detection of giardial antigens in patient stool specimens. Serologic tests have proven to be of little value in giardial diagnosis because there is little correlation between positive anti-giardia antibody titers and the presence of active giardial infection. Cross-reactions with microbial antigens have also caused problems.

Stool antigen detection tests have been more successful. Craft, J. C., et al., *J. Infect. Dis.* 145:499–504 (1982) report the use of counterimmunoelectrophoresis (CIE) with rabbit antiserum prepared against *G. lamblia* cysts for detection of *G. lamblia*-specific antigens in stool. Vinayak, V. K., et al., *Pediatr. Infect. Dis.* 4:383–386 (1985) teach use of rabbit antiserum against trophozoites grown in culture in a CIE test for Giardia antigens in patients' stools. Ungar, L. P., et al., *J. Infect. Dis.* 149:90–97 (1984) describe use of rabbit and goat antisera prepared against trophozoites grown in culture in the development of an antigen-capture enzyme-linked immunosorbent assay (ELISA) for detecting Giardia antigens in stool. Green, E. L., et al., *Lancet ii*:691–693 (1985) similarly describe an antigen-capture ELISA using antisera prepared against trophozoites grown in culture as well as cysts. Similarly, Nash, T. E., et al., *J. Clin. Micro.* 25:1169–1171 (1987); Janoff, E. N., et al., *J. Clin. Micro.* 27:431–435 (1989); Stibbs, H. H., et al., *J. Clin. Micro.* 26:1665–1669 (1988) have described more recently immunoassays for detection of Giardia infection.

Despite good sensitivity, the above tests pose certain problems. First, such tests usually employ polyclonal polyspecific antibodies against the whole *Giardia lamblia* trophozoite and/or cyst, raising concerns of cross-reactivity with other gastrointestinal parasites. Further, most antigens targeted in these polyclonal polyspecific antibody based assays are labile to conventional laboratory fixatives and media used for collection, transport, and storage of stool specimens destined for O&P microscopic examination or stool culture. Such immunoassays thus require the use of untreated stool specimens and thus limitations are imposed upon existing stool collection procedures.

Identification of a *Giardia lamblia*-specific stool antigen (GSA 65) useful in the diagnosis of giardiasis has been reported previously, Rosoff, J. D., et al., *J. Clin. Micro.* 23(5):905–910 (1986) (I). The antigen was further characterized physically and chemically. Rosoff, J. D., et al., *J. Clin. Micro.* 24(6):1079–1083 (1986) (II). Notwithstanding the foregoing publications, the general procedures as described in these papers fail to teach certain key aspects of the protocol for obtaining GSA 65. These key steps, to be described in detail below, fully enable one of ordinary skill to isolate GSA 65 and produce monospecific polyclonal antibodies thereto. The disclosures of each of the above-identified publications are herein incorporated and made part of this disclosure subject to the acknowledged defects of both.

SUMMARY OF THE INVENTION

In accordance with the present invention, a dissociate-stable complex of the glycoprotein GSA 65 with mammalian-based antibody to mammalian *G. lamblia* cyst has now been discovered. This complex constitutes one aspect of this invention.

In a second aspect, it has been discovered that this stable complex is formed by contacting an impure solution of GSA 65 antigen with a substrate having linked thereto antibodies to mammalian *G. lamblia* cysts thereby forming a precipitin comprising the bound complex; rinsing impurities from the substrate; drying the substrate at a temperature from about 65° to 80° C. for about 30–60 minutes; and thereafter contacting the substrate with an acidic aqueous alcohol mixture to partially denature the bound complex and give rise to a precipitin comprising a stable GSA 65 *G.-lamblia* cyst antibody complex.

The stable GSA 65-cyst antibody complex can be used to give rise to a specific immune response in mammals. This response leads to the production of polyclonal antibodies which are monospecific to GSA 65 antigen. These polyclonal monospecific anti-GSA 65 antibodies are another aspect of this invention.

Yet additional aspects of this invention comprise using these polyclonal antibodies, and kits based thereon, in assays for *G. lamblia* infection in mammals.

In a further aspect, these polyclonal antibodies can be immobilized to a substrate to give rise to a specific immunosorbant substrate which will, for the first time selectively isolate in pure form the underlying GSA 65 antigen; which antigen is another aspect of this invention.

The isolated GSA 65 Giardia-specific stool antigen of the invention and the monospecific anti-GSA 65 antibodies thereto are useful in the coprodiagnosis of giardiasis. Identification and characterization of such an antigen allows for the standardization of assays for Giardia antigens in stool.

The result is a fast and straightforward method of diagnosing giardiasis capable of detecting GSA 65 in stool that is adjudged negative by standard O&P examination. Further, GSA 65 reveals almost no cross-reactivity with other intestinal protozoa. The method of the present invention is also not adversely affected by traditional fixatives and media used for collection, transport and storage of stool specimens.

Other features and advantages of the invention will be apparent from the following description of the preferred embodiments thereof and from the claims.

DESCRIPTION OF THE PREFERRED EMBODIMENTS

Isolation and Identification of Giardia lamblia-Specific Stool Antigen (GSA 65)

As described in the above-identified publications (I), (II), parasite cultures of trophozoites of G. lamblia (WB strain, ATCC 30957), Trichomonas vaginalis (local isolate HMC-1, my designation), Pentatrichomonas hominis (Diamond strain, ATCC 30000), and Entamoeba histolytica (NIH 200 strain, ATCC 30458) were axenically cultured at 37° C. as described by Einfeld, D. E., et al., Infect. Immun. 46:377–383 (1984), Torian, B. E., et al., Infect. Immun. 46:152–158 (1984), and Diamond, L. S., et al., Trans. R. Soc. Trop. Med. Hyg. 72:431–432 (1978). All cultures were grown in antibiotic-free medium. Leishmania donovani promastigotes were donated by Steven Reed, Issaquah Health Research Laboratory, Issaquah, Wash. Candida albicans was donated by Paula Sundstrom of the University of Washington grown on Saboraud agar in vertical, loosely capped borosilicate tubes at 25° C.

Rabbit polyclonal antiserum was prepared against stool cysts recovered by the following procedure. Fresh, refrigerated stool specimens, previously verified to be G. lamblia-positive by microscopy, were suspended in 4 to 5 volumes of distilled water, filtered through two layers of cheesecloth, and centrifuged at 500 to 700×g for 5 min. The supernatant was discarded, and the pellet was suspended in distilled water containing 0.5% Tween 80 to remove lipids. The suspended material was repeatedly washed in 0.5% Tween 80 until the supernatant remained clear after centrifugation. The pellet was then suspended in distilled water and layered upon an equal volume of a 0.85M sucrose solution. Tubes were centrifuged for 20 min. at 500×g, and cysts from the water-sucrose interface were removed, washed repeatedly with distilled water, and then centrifuged at 900×g for 2 min. Harvested cysts were stored in an aqueous solution of (per milliliter) 200 U of penicillin G, 200 ug of streptomycin, 50 ug of gentamicin, and 5 ug of amphotericin B in 1.5 ml polypropylene tubes at 4° C. Rabbits were immunized intramuscularly at several sites with 2 ml of intact cysts at a concentration of $5 \times 10^5$ cells per ml mixed with 2 ml of Freund incomplete adjuvant. After 3 weeks, the rabbits were boosted intravenously twice weekly with increasing doses of cysts (0.1 ml, 0.2 ml, 0.3 ml and 0.4 ml doses at a concentration of $5 \times 10^5$ cysts per ml). One week after the last booster injection, the animals were anesthetized and bled by cardiac puncture. The serum was stored at –20° C. Mammals other than rabbits may also be used for antiserum preparation.

Preparation of antigens for electrophoretic techniques were prepared as follows:

(i) Stool eluates. G. lamblia cyst-positive and control stools were collected from various clinical and private sources. Approximately 1 g of non-Formalin-fixed (fresh) stool was added to 3 ml of distilled water, mixed well by stirring, and centrifuged at 900×g for 5 min. Supernatants were stored at –20° C.

(ii) G. lamblia cysts. Previously purified G. lamblia cysts were suspended in 10 mM phosphate buffer (pH 6.8) containing 0.1% Triton X-100 at a concentration of $2 \times 10^6$ to $3 \times 10^6$ cysts per ml and were sonicated on ice with a minimum of eight 10-s pulses from a Branson cell disrupter. Complete disruption of the cyst preparation was verified by light microscopy. Sonicated preparations were centrifuged at 12,000×g for 6 min, and the supernatant was assayed for protein by the method of Bradford, M. N., Anal. Biochem. 72:248–254 (1976). Supernatants were diluted to a final protein concentration of 1 to 2 mg/ml and stored at –20° C. until needed.

(iii) Trophozoites of G. lamblia, T. vaginalis, P. hominis, and E. histolytica. After harvest in late log phase, trophozoites were chilled on ice for 20 min, pelleted by centrifugation at 800×g, and washed four times in cold phosphate-buffered saline (PBS) or cold saline-1% glucose. After washing, cultures were suspended in 10 mM phosphate buffer (pH 6.8) containing 0.1% Triton X-100 and sonicated with six 10-s bursts on ice. Particulate matter from sonic extracts was removed by centrifugation at 12,000×g for 6 min, and the supernatant was assayed for protein by the method of Bradford, supra. Supernatants were diluted to a final protein concentration of 1 to 2 mg/ml and were stored at –20° C. until needed.

(iv) G. lamblia-specific antigen from stool eluates. G. lamblia-specific antigen present in eluates of stools from G. lamblia-positive patients was partially purified by the following procedure before affinity chromatography. Stool (10 g) was suspended in 500 ml of distilled water and centrifuged at 10,000×g for 20 min. The pellet was discarded, and the supernatant was subjected to 50% ammonium sulfate precipitation followed by centrifugation at 10,000×g for 20 min. The supernatant was discarded, and the pellet was suspended in distilled water to the original volume and subjected to a second 50% ammonium sulfate precipitation, followed by centrifugation at 10,000×g for 20 min. The pellet was suspended in distilled water, extensively dialyzed at 4° C. against distilled water containing 0.1% ammonium hydroxide, and lyophilized. The dried material was suspended in 5 ml of 50 mM Tris buffer (pH 8.2) containing 1 mM phenylmethylsulfonyl fluoride and 5 mM EDTA and stored at −20° C. until needed for affinity chromatography.

Electrophoretic Techniques

CIE with polyclonal anti-cyst antisera was used to verify the presence of *G. lamblia*-specific antigen in *G. lamblia* cyst-positive stool samples as described by Kenny, G. E., pp. 105–111 in Coonrod, J. D., et al., *Direct Detection of Microorganisms In Clinical Samples* Academic Press, Inc. (1983). By using glass slides (43 by 43 mm or 1 by 3 in [2.54 by 7.62 cm]) covered with 2.5 ml of 0.9% agarose in electrophoresis buffer (20 mM Ches, 16 mM Bicine, 0.05% Triton X-100 [pH 8.86]), two 3 mm-diameter wells separated by 5 mm were punched in the agarose, oriented parallel to the electric field. The well closest to the anode was filled with 10 ul of either rabbit anti-cyst antiserum or rabbit monospecific antiserum prepared against the isolated *G. lamblia*-specific stool antigen. The well closest to the cathode was filled with 10 ul of aqueous eluate (one part stool to three parts distilled water) of stool of a giardiasis patient or of a control patient. Electrophoresis with a field strength of 5 V/cm was applied for 90 min. Before being dried and stained with Coomassie blue R-250, plates were washed for 24 h in Tris-buffered saline (10 mM Tris, 150 mM NaCl [pH 7.2]), followed by a 24-hour rinse in distilled water.

Antigen for monospecific antibody production was isolated by using line immunoelectrophoresis as described by Axelsen, N. H., et al., *Scand. J. Immunol.*, Suppl. 1, 2:47–77 (1973). Glass slides (43 by 43 mm) were covered with 2.5 ml of 0.9% agarose in electrophoresis buffer. The upper two-thirds of the agarose was excised and replaced with 1.6 ml of 0.9% agarose containing 2.5% of the IgG fraction of rabbit anti-cyst antiserum. A trough (3 by 35 mm) was cut in the lower one-third of the agarose and was subsequently filled with 50 to 70 ul of stool eluate from patients previously shown to be *G. lamblia*-positive by microscopy and Giardia antigen-positive by CIE, as described above, by using anti-cyst antiserum. Electrophoresis with a field strength of 1 V/cm was applied for 15 h. Lines of antibody-GSA 65 complex/precipitin form on the slides.

Immediately following electrophoresis, slides were washed in Tes-Buffered Saline (TBS) for 2 days on a rotary shaker with six changes of buffer. The slides were subsequently washed with distilled water for 1 day on a rotary shaker with 3 changes of water.

Following the washes, the slides were dried in an oven at 65°–80° C. until the agarose was dried to a thin film (30–60 min). Air drying is not recommended; oven drying allows a more durable surface for staining steps. Care must be taken not to overdry these slides or the agarose will crack and sometimes peel from the glass.

Following oven drying, slides were then stained for 10 minutes in staining solution (0.5% Coomassie blue R-250 in acid, for example acetic or trichloroacetic acid (TCA), preferably acetic acid, in the range of 10–20% (v/v), preferably 10%; alcohol, such as methanol, ethanol, or isopropanol, preferably ethanol, in the range of 35–50% (v/v), preferably 45%; and distilled water) and de-stained for 1–2 min by rigorously shaking in de-staining solution (acid for example acetic or trichloroacetic acid (TCA), preferably acetic acid, in the range of 10–20% (v/v), preferably 10%; alcohol, such as methanol, ethanol, or isopropanol, preferably ethanol, in the range of 35–50% (v/v), preferably 45%; and distilled water). Pure water-based stain/de-stain solutions (those with only 0.5% Coomassie blue and water) will not produce a slide preparation that will allow anti-GSA 65 antiserum production. Water-based stains most often will not allow visualization of antibody-GSA 65 precipitins in the agarose bed, and hence precipitin extraction is either hindered or impossible. Furthermore, even if one is fortunate enough to extract precipitins from "water-based" stained gels, this material is not antigenic when injected in animals.

GSA 65 is highly soluble and likely dissociates from the antibody in these preparations before antigen presentation in the host can take place. No anti-GSA 65 titers are observed in animals immunized with "water-based" stained gels. Acetic acid/ethanol-based stains appear to irreversibly denature the GSA 65/antibody precipitin complex so that it does not dissociate and remains insoluble even after injection into the animal. Because this material remains insoluble, it is well presented to the animal's immune system and excellent GSA 65 antibodies are raised.

Monospecific antiserum against *G. lamblia*-specific antigen present in stool eluates was prepared by a procedure described by Alexander, A. G., et al., *Infect. Immun.* 15:313–321 (1977). Precipitin arcs from agarose line-immunoelectrophoresis plates, supra, were excised from 200 plates as described by Norrild, B., et al., *Anal. Biochem.* 81:432–441 (1977). For the initial injection, precipitin arcs in agarose were emulsified in Freund complete adjuvant and injected intradermally at multiple sites on the neck and upper back of two New Zealand White rabbits. After 3 weeks, a series of weekly intramuscular injections of precipitin arcs emulsified in Freund incomplete adjuvant was begun and was continued for about 3 months. Rabbits were exsanguinated as previously described, and sera were stored at −20° C. Immunoglobulin G (IgG) fractionation of antisera was performed by using a protein A-Sepharose column (Pharmacia Fine Chemicals, Piscataway, N.J.) as described by Goding, J. W., *J. Immunol Methods* 13:215–216 (1976).

To obtain profiles of the precipitable antigens found in *G. lamblia*-positive stool eluates, crossed-immunoelectrophoresis techniques were employed. These techniques were used to characterize the electrophoretic mobility of the stool antigen, to check for cross-reactivity of the monospecific antiserum with antigens from the trophozoite and cyst preparation, and to determine whether anti-trophozoite antiserum could precipitate similar Giardia antigens from stool eluate. Crossed immunoelectrophoresis, tandem crossed immunoelectrophoresis, and intermediate gel crossed immunoelectrophoresis, as described by Axelsen, V. H., et al., *Scand. J. Immunol.*, Suppl. 1, 2:47–77 (1973), were performed on glass slides (43 by 43 mm) covered with 2.5 ml of 0.9% agarose in electrophoresis buffer. For first-dimensional electrophoresis, a field strength of 5 V/cm was applied for 60 min. Bovine serum albumin (BSA) (3 ug) was added to the antigen to be used as a migration standard. Before electrophoresis in the second dimension, a gel containing 2.5% rabbit antiserum and 0.25% rabbit anti-BSA antiserum was poured above the 1 cm strip containing the separated antigen preparation, and electrophoresis was performed for 15 h at 1 V/cm. Washing and staining procedures were the same as those used in CIE.

Sodium dodecyl sulfate-polyacrylamide gel electrophoresis (SDS-PAGE) was used for characterization of the *G. lamblia*-specific antigen in the immunoadsorbent column eluates and in *G. lamblia* trophozoite and cyst sonic extracts. SDS-PAGE was performed basically as described by Laemmli, U. K., *Nature* (London) 227:680–685 (1970). A 5% stacking gel and an 8% separating gel were used. Immunoadsorbent column fractions, trophozoite sonic extracts, and cyst sonic extracts were mixed with an equal volume of sample buffer consisting of 4% sodium dodecyl sulfate, 20% glycerol, 10% 2-mercaptoethanol, 0.004% bromophenol blue, and 0.2M Tris hydrochloride buffer (pH 6.8) and boiled for 2 min before addition to the sample slots. After electrophoresis, some unstained slabs were used for Western blotting. Others were silver stained for protein detection by the method described by Merril, C. R., et al., *Science* 211:1437 (1981) or stained for carbohydrate detection by the periodate oxidation-silver stain method described by Tsai, C. M., et al., *Anal. Biochem.* 119:115–119 (1982).

Western blotting was performed by transferring antigens separated by SDS-PAGE to nitrocellulose paper. The antigens were analyzed by the method of Towbin et al., *Proc. Natl. Acad. Sci. USA* (1979) 76:607–610 as modified by Burnette, W. N., *A. Anal. Biochem* 112:195–203 (1981). After transfer, nitrocellulose sheets were incubated for 1 h at room temperature in blocking buffer (160 mM NaCl, 5 mM 4-sodium EDTA, 0.25% gelatin, 0.1% Tween 20 in 10 mM TES [N-tris(hydroxymethyl)methyl-2-aminoethanesulfonic acid] buffer [pH 7.3]). Sheets were transferred to fresh blocking buffer containing 0.32% rabbit antiserum, incubated with slow shaking for 1 h and then washed repeatedly in 0.02M PBS (pH 7.6) containing 0.5% Tween 20 (PBS-T). The sheets were placed in fresh blocking buffer containing 0.1% peroxidase-conjugated goat anti-rabbit IgG (Antibodies, Inc., Davis, Calif.) for 1 h at 25° C. and then washed six times in PBS. Nitrocellulose sheets were developed by the addition of freshly prepared 0.06% (w/v) 4-chloro-1-naphthol (Sigma Chemical Co., St. Louis, Mo.) and 0.01% hydrogen peroxide in PBS.

Affinity-purified GSA 65 was analyzed by isoelectric focusing (IEF) with agarose as described by Marine Colloids, Marine Colloids, Technical Bulletin, Marine Colloids, Rockland, Me. (1982) with the following modifications. The agarose gels contained 1% IsoGel agarose and 3% ampholyte (IsoGel ampholyte [pH 3.0 to 10.0]; Marine Colloids, Rockland, Me.). No other additives, such as sorbitol, were used. Gels were cast to a thickness of 1 mm at 65° C. and stored overnight at 4° C. until use.

IEF was accomplished with a thermally controlled Isobox and PS-2500 programmable power supply (both from Hoefer Scientific Instruments, San Francisco, Calif.). An application mask allowed samples of 4 ul to remain in contact with the gel surface for 10 to 20 min to allow sample absorption before the run. The anolyte was 0.5M acetic acid and the catholyte was 1.0M NaOH. Samples were initially electrophoresed for 5 min at 500 V. Then, the sample application mask was removed and IEF was continued at a constant power of 7 W for 25 min. The voltage was then increased to 2,000 V for 5 min before termination of the run. The gel was immediately removed from the Isobox and subjected to precipitation in trichloroacetic acid.

Immunoadsorbent chromatography was performed by binding 60 mg of the IgG fraction of the monospecific rabbit antiserum to 2 g (dry weight) of CNBr-Sepharose 4B (Pharmacia) in 20 ml of coupling buffer (0.1M NaHCO$_3$ [pH 8.5] containing 0.5M NaCl), as recommended by the manufacturer. Excess active groups on the gel were blocked by incubation of the slurry overnight at 4° C. with 40 ml of 0.1M glycine in coupling buffer. The gel was transferred to a 10 ml column and washed alternately with coupling buffer and 0.1M acetate buffer (pH 4.0) containing 0.5M NaCl. The gel was prepared for use by washing in PBS-T. Partially purified *G. lamblia*-specific antigen from stool eluates and *G. lamblia* cyst and trophozoite sonic extracts, prepared as described above, were applied to separate immunoadsorbent columns and allowed to react for 2 h at 4° C. Unadsorbed antigens were removed by washing the column with 100 ml of PBS-T. Non-specifically adsorbed antigens were eluted by using 50 ml of PBS-T containing 1M NaI. The more avidly bound Giardia antigen was then eluted with 25 ml of PBS-T containing 3M NaI, exhaustively dialyzed against distilled water at 4° C., and lyophilized or concentrated by ultrafiltration. Concentrates were analyzed by crossed immunoelectrophoresis, SDS-PAGE, and Western blotting.

An immunofluorescence assay was performed by first washing purified *G. lamblia* cysts and all cultured protozoan trophozoites were washed three times in cold sterile saline-1% glucose before use in the immunofluorescence assay. The concentration of cells was adjusted to $10^6$ per ml in sterile glucose, and 10 ul of each was applied to multispot, Teflon (E.I. Du Pont de Nemours & Co., Inc., Wilmington, Del.)-coated glass microscope slides, air dried, and then fixed for 5 min in acetone. Assay by immunofluorescence was also performed with smears of feces containing *Blastocystis hominis* or cysts of *E. histolytica*, with oocysts of Cryptospiridium purified from cattle, and with cysts of *Chilomastix mesnili* prepared from human stools by ethyl acetate-Formalin concentration as described by Brown, H. W., et al., *Basic Clinical Parasitology*, 5th ed., Appleton-Century-Crofts, Norwalk, Conn. Assay by indirect immunofluorescence was performed by standard methods in humid chambers at 37° C. using 1 h-incubations with both the primary and secondary antibodies. The secondary, fluorescein-conjugated antibody used was fluorescein-labeled goat anti-rabbit IgG (IgG fraction) (Cappel Division, Cooper Biomedical, Inc., West Chester, Pa.) diluted 1:40 in PBS containing rhodamine-albumin counterstain (Difco Laboratories, Detroit, Mich.) diluted 1:80. Slides were mounted with fluorescence mounting medium (Difco) and viewed by using epifluorescence. Photographs were taken at x190 magnification on Kodak Ektachrome 160 Tungsten film (Eastman Kodak Co., Rochester, N.Y.).

EXAMPLE 1

Isolation of GSA 65

Figure 1:
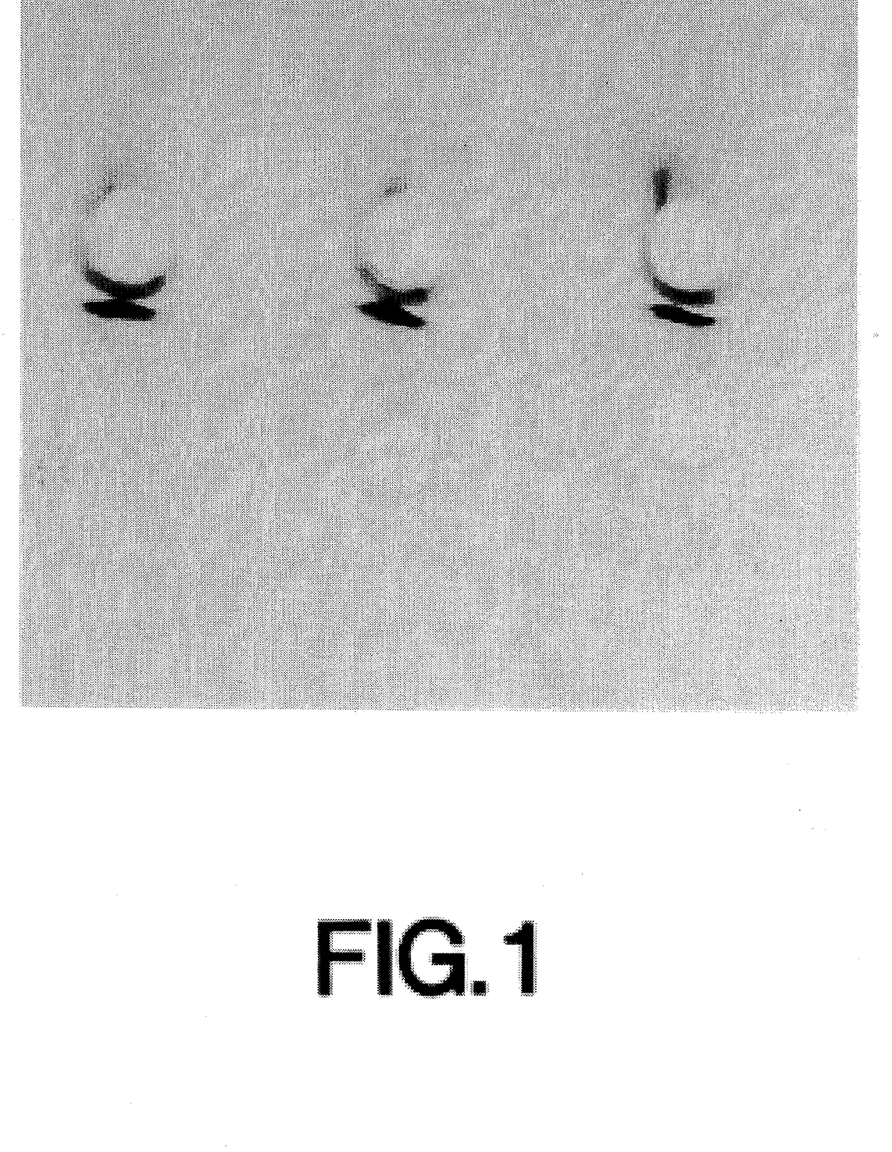
FIG. 1 is a photograph showing CIE analysis of three Giardia lamblia-positive stool eluates by using anti-cyst antiserum.

CIE performed as described above was used to determine whether anti-cyst antiserum was capable of detecting antigens in Giardia cyst-positive stools. As seen in FIG. 1, well-defined double precipitin line (doublet) was visible for stool eluates from 36 of 40 Giardia cyst-positive stool eluates, but was not visible in 10 cyst-negative controls derived from patients without clinical symptoms. With anti-cyst antiserum, precipitin lines were seldom visible before washing and staining. Use of the IgG fraction of the anti-cyst antiserum changed the doublet appearance of the precipitin to that of a single line. All of the 36 stool eluates shown to be positive by CIE with anti-cyst antiserum were also shown to be positive by CIE with monospecific antiserum as seen in Table 1, and showed the same characteristic anodal precipitin arcs.

TABLE 1

Cross-Reactivity Studies of Anti-GSA 65
Antiserum as Assessed by CIE

| Stool eluate | No. of positive reactions/ total no. of reactions |
|---|---|
| G. lamblia only; patient symptomatic | 36/40 |
| Intestinal parasites other than G. lamblia | 4/31 |
| Gastrointestinal symptoms but negative by O&P exam[a] for parasites | 2/18 |
| No G. lamblia; asymptomatic, nonexposed controls | 0/10 |

[a]O&P exam = ovum and parasite stool examination.

The electrophoretic mobility and purity of the antigen precipitated in CIE were assessed by crossed immunoelectrophoresis. When 10 stool eluates from patients previously verified as G. lamblia-positive by microscopy and CIE were used in crossed immunoelectrophoresis against the monospecific anti-GSA 65 antiserum or against the IgG fraction of the anti-cyst antiserum, a single peak with a mobility of 1.26 (migration distance in relation to BSA, assigned a value of 1.0) was observed. The peak height of this precipitin was varied from sample to sample, likely reflecting variations in the quantity of antigen in the stools. Using the same 10 stool eluates, no precipitin peaks were observed when rabbit anti-trophozoite antiserum or preimmune rabbit serum was used in crossed immunoelectrophoresis. Comparative analysis of these stool eluates by tandem crossed immunoelectrophoresis using anti-cyst antiserum revealed that the precipitable antigens from each stool specimen were immunologically identical; i.e., immunoprecipitates from different stools were fused in a single uneven line and no spurs were seen. Intermediate gel crossed immunoelectrophoresis of G. lamblia-positive stool eluates using anti-cyst antiserum with monospecific antiserum in the intermediate gel produced a single precipitin peak, suggesting that the monospecific and the anti-cyst antisera were precipitating the same antigen.

Figure 2:
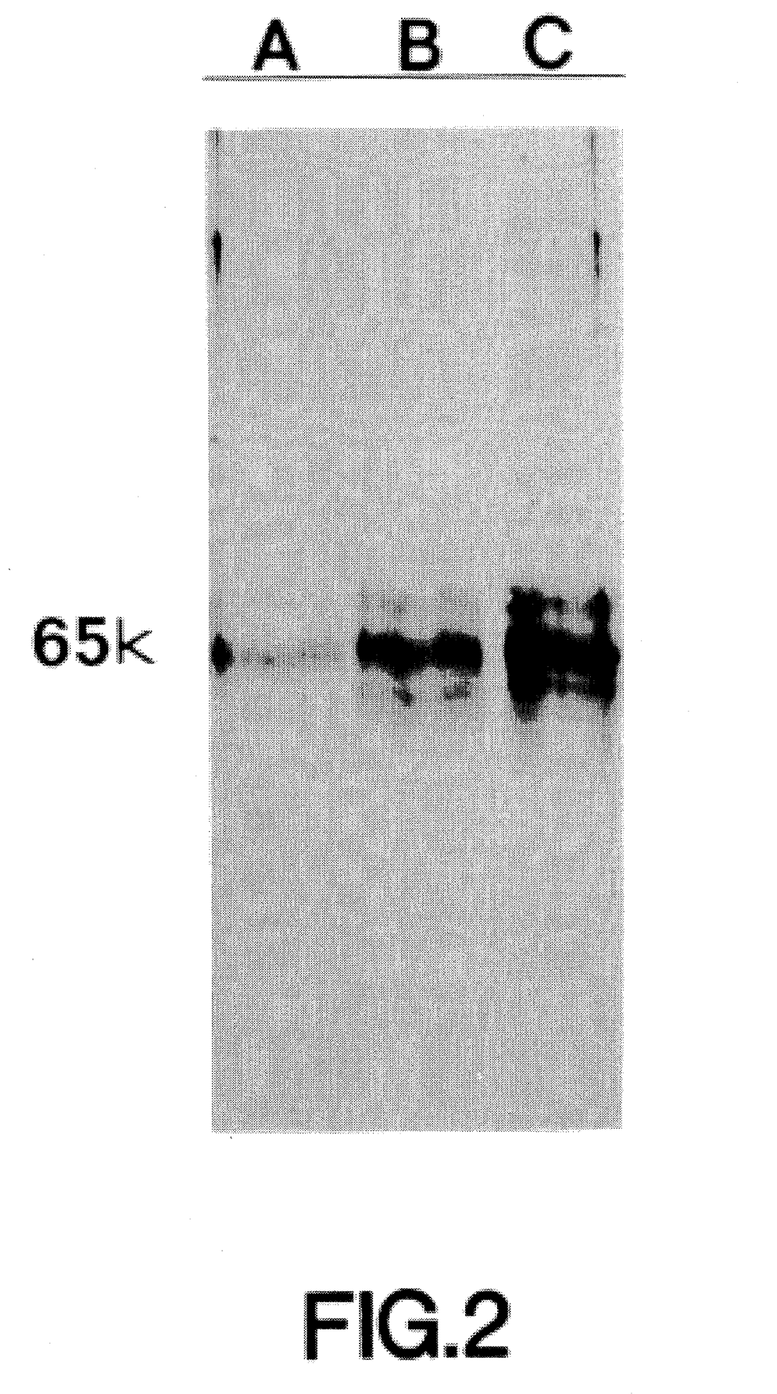
FIG. 2 is a photograph of immunoblots of affinity-purified preparations of GSA 65 from trophozoite sonic extracts (lane A), cyst sonic extracts (lane B), and purified G. lamblia-positive stool eluate (lane C) reacted with monospecific anti-GSA 65 antiserum.
Figure 3:
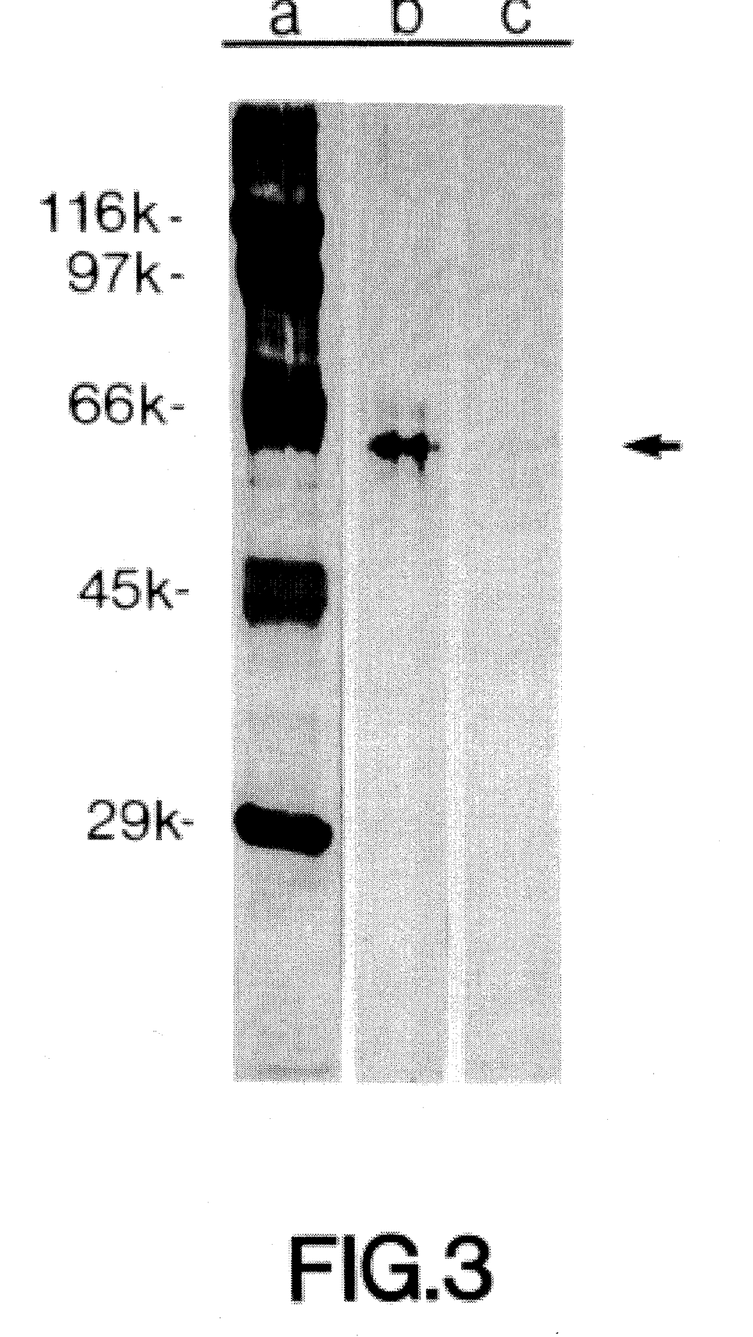
FIG. 3 is a photograph of SDS-PAGE Western blots of affinity-purified GSA 65. Lane a contains protein molecular weight standards; lane b contains GSA 65 as detected by 0.327% monospecific rabbit anti-GSA 65 antiserum; lane c contains GSA 65 as detected by 0.32% rabbit anti-whole G. lamblia trophozoite antiserum.

To determine the approximate molecular weight(s) of the stool-derived antigen and also to determine whether this antigen could be identified in G. lamblia cysts and trophozoites, sonic extracts from trophozoites grown in culture, purified cyst sonic extracts, and partially purified antigen from cyst-positive stool eluates were individually passed over Sepharose affinity columns prepared with the IgG fraction of the monospecific antiserum. SDS-PAGE followed by Western blotting of reconcentrated affinity column eluates revealed that all of the eluates had identical banding patterns as seen in FIG. 2. Each demonstrated a band of a molecular weight of approximately 62,000 to 70,000, with a majority of 65,000 with light smearing from 62,000 to 68,000 above and below the main band; hence, this antigen is referred to as as GSA 65 (Giardia stool antigen 65). Crossed immunoelectrophoresis of affinity column eluates against monospecific antiserum revealed precipitin peaks of the same electrophoretic mobility (1.26) as those seen by using cyst-positive stool eluates. Crude sonic extracts of both trophozoites and cysts also were found to contain enough GSA 65 to be detected with the monospecific antiserum by CIE and by crossed immunoelectrophoresis.

EXAMPLE 2

Specificity Testing

The species specificity of GSA 65 was assessed by CIE on stool eluates from patients with various protozoan and other parasitic diseases and on a variety of species of cultured protozoa and cultured C. albicans; specificity was assessed also by immunofluorescence as described above, in all cases using the monospecific anti-GSA 65 antiserum as prepared above. The results are shown in Table 2.

TABLE 2

Reactivity of Cultured Organisms for
Anti-GSA 65 Antiserum as Assessed by CIE

| Cultured organism (cell type) | Reactivity[a] |
|---|---|
| G. lamblia (trophozoites) | + |
| P. hominis (trophozoites) | − |
| T. vaginalis (trophozoites) | − |
| E. histolytica (trophozoites) | − |
| L. donovani (promastigotes) | − |
| C. albicans (yeasts and germ tubes) | − |

[a]+ = positive reaction; − = negative reaction.

A total of 49 G. lamblia-negative stool eluates (controls) were assayed for the presence of GSA 65 by CIE with the monospecific antiserum against this antigen (Table 1, infra). Of 31 stool eluates from patients with other non-Giardia protozoan and helminth parasites, 4 were positive for the antigen. Of these positives, one stool contained Entamoeba coli, one contained E. histolytica, and two contained Entamoeba nana. However, four of five E. histolytica-positive stools were CIE negative, as were three of four E. coli- and four of six E. nana-containing stools. Of 18 stool eluates from patients with gastrointestinal symptoms who were negative for intestinal parasites by microscopic examination, 2 were positive for the presence of GSA 65. Sonic extracts of cultured P. hominis, E. histolytica, T. vaginalis, C. albicans, and L. donovani promastigotes run in CIE were negative for GSA 65. Sonic extracts of G. lamblia trophozoites run as a positive control yielded precipitin lines, as expected.

In immunofluorescence studies, monospecific antiserum reacted strongly with purified G. lamblia cysts. Cyst walls fluoresced brightly, and this fluorescence precluded visualization of internal morphology. Fluorescence of the cyst wall was negligible when cysts were reacted with preimmune serum. Giardia trophozoites did not fluoresce when reacted with monospecific antiserum or preimmune serum, despite the fact that trophozoites were shown to contain GSA 65 by affinity chromatography and CIE. Monospecific antiserum failed to react with cultured trophozoites of E. histolytica, P. hominis, T. vaginalis, and C. albicans. Fecal smears containing cysts of both E. histolytica and Entamoeba hartmanni and preparations of C. mesnili cysts, Cryptosporidium oocysts, and B. hominis were also nonreactive.

EXAMPLE 3

Assessment of GSA 65 Purity

Figure 4:
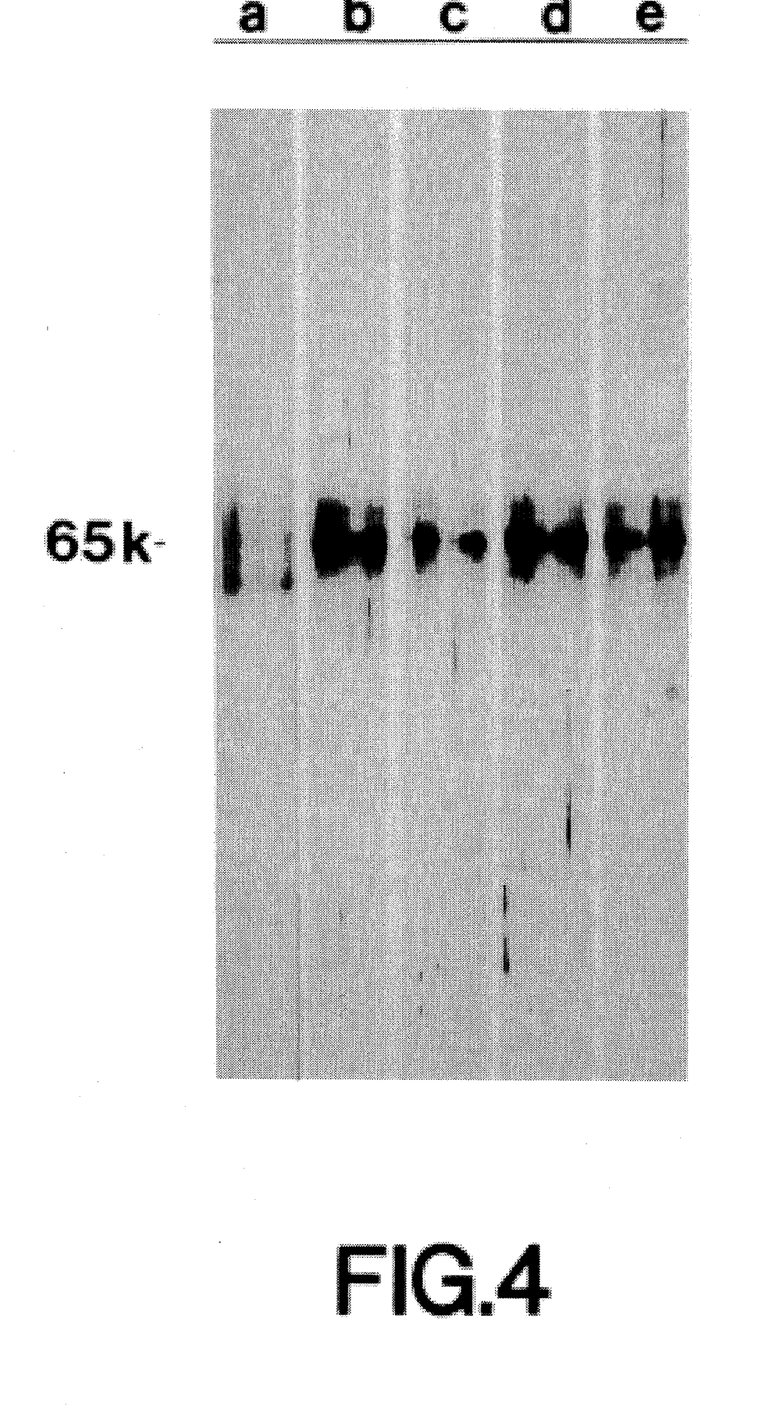
FIG. 4 is a photograph of SDS-PAGE Western blots of proteolytically treated GSA 65. Lanes a and b, undigested (control) GSA 65; lane c contains trypsin-digested GSA 65; lane d contains chymotrypsin-digested GSA 65; lane e, protease-digested GSA 65.

Before characterization experiments, the purity of affinity-purified GSA 65 was assessed by SDS-PAGE, followed by Western blotting and silver staining. Nitro-cellulose sheets were developed with antitrophozoite antiserum and monospecific anti-GSA 65 antiserum to assess whether trophozoite antigens in addition to GSA 65 had nonspecifically bound and been eluted from the affinity column. A single diffuse band characteristic of GSA 65 developed at a molecular weight of 65,000, as seen in FIG. 4. Periodic acid-Schiff silver stains of polyacrylamide gels also revealed a single dark staining region in the 65,000-molecular-weight range. No contaminants were noted in either technique.

EXAMPLE 4

Characterization of GSA 65

The chemical nature of GSA 65 was characterized by proteolytic digestion, boiling, periodate oxidation, and lectin binding experiments. The antigen was boiled for 10 min to assess its heat stability. Stability under oxidizing conditions was assessed by periodate treatment: a solution of 100 mM $NaIO_4$ was prepared in 20 mM acetate buffer (pH 4.5), and 30 ul was added to 30 ul of antigen in a polypropylene centrifuge tube. Controls received 30 ul of buffer alone. Oxidation was carrier out at 4° C. for 24 h in the dark. The reaction was immediately quenched with 30 ul of 0.5M $NaBH_4$, followed by drying under $N_2$ for 2 h. The proteolytic sensitivity of GSA 65 was determined by incubation with trypsin, chymotrypsin, and protease (all from Sigma Chemical Co., St. Louis, Mo.). Trypsin and chymotrypsin were used at an enzyme concentration of 200 ug/ml in 0.1M Tris hydrochloride buffer (pH 8.0). GSA 65 was digested for 24 h at 37° C. Protease was used at a concentration of 10 mg/ml in 0.1M Tris hydrochloride (pH 8.0) containing 1 mM $CaCl_2$. GSA 65 was incubated for 15 min at 37° C., followed by digestion at 60° C. for 24 h. controls received 0.1M Tris hydrochloride alone. All digestions were terminated by boiling for 3 min. The effect of these treatments was evaluated by sodium dodecyl sulfate-polyacrylamide gel electrophoresis (SDS-PAGE), followed by Western blotting with monospecific rabbit anti-GSA 65 antiserum (infra).

Figure 5:
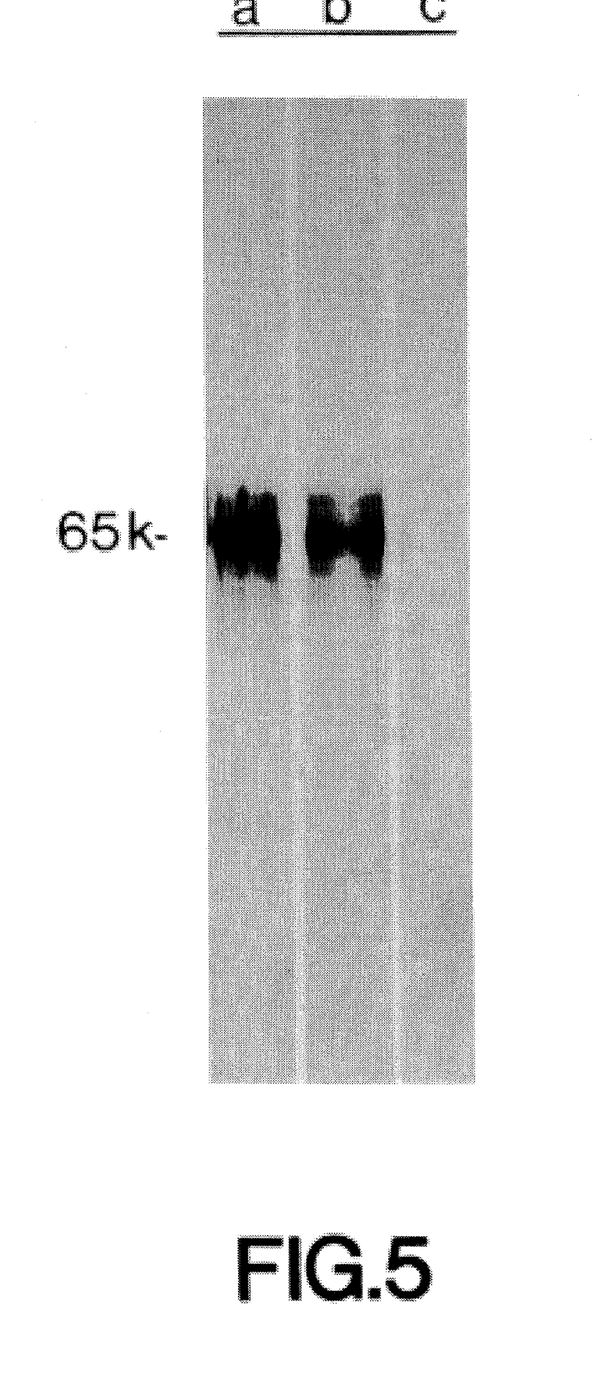
FIG. 5 is a photograph of SDS-PAGE Western blots of heat-treated and oxidized GSA 65 as detected by 0.32% monospecific rabbit anti-GSA 65 antiserum. Lane a contains untreated (control) GSA 65; lane b contains GSA 65 boiled for 10 min; lane c, periodate-treated GSA 65, followed by $NaBH_4$ reduction.

As seen in FIG. 5, affinity-purified GSA 65 was not labile after proteolytic digestion with trypsin, chymotrypsin, or protease. After proteolytic digestion, GSA 65 retained its reactivity with monospecific antiserum. All digests retained the same Western blotting patterns as the undigested controls. GSA 65 was labile after periodate oxidation but stable after boiling. After oxidation with $NaIO_4$ and reduction with $NaBH_4$, GSA 65 lost immunoreactivity and could not be detected in immunoblots. After boiling, GSA 65 retained it immunoreactivity and electrophoretic mobility in Western blots. Controls showed no change in immunoreactivity, mobility, or molecular weight.

The carbohydrate composition of GSA 65 was assessed in lectin-binding studies as described above. A sample (5 ug) of GSA 65 was applied to pieces of (1.5 by 1.5 cm) of nitrocellulose, The nitrocellulose pieces were incubated for 12 h at 23° C. in TBS-CS (10 mM Tris hydrochloride, 150 mM NaCl [pH 8.0], 10% fetal calf serum) to block the remaining binding sites. The TBS-CS solution was replaced with freshly prepared concanavalin A-peroxidase, castor bean agglutinin-peroxidase (RCA-I), or wheat germ agglutinin-peroxidase (all from Sigma), solutions at 50 ug/ml in TBS-CS containing 5 mM $CaCl_2$ and 5 mM $MgCl_2$. Each strip was incubated for 30 min at 23° C., followed by three 5-min washes in TBS-CS to remove unbound lectin-peroxidase conjugates. Bound peroxidase was detected by the addition of a freshly prepared solution of 0.06% (w/v) 4-chloro-1-naphthol (Sigma)—0.01% hydrogen peroxide in 0.1M Tris buffer. The specificity of binding was assessed by the addition of the appropriate competing carbohydrate to the reaction mixture at a concentration of 100 mM.

In the lectin-binding studies, GSA 65 bound RCA but not concanavalin A-peroxidase or wheat germ agglutinin-peroxidase. RCA binding was specific and could be blocked by the addition of 100 mM D-(+)-galactose to the reaction mixture.

Figure 6:
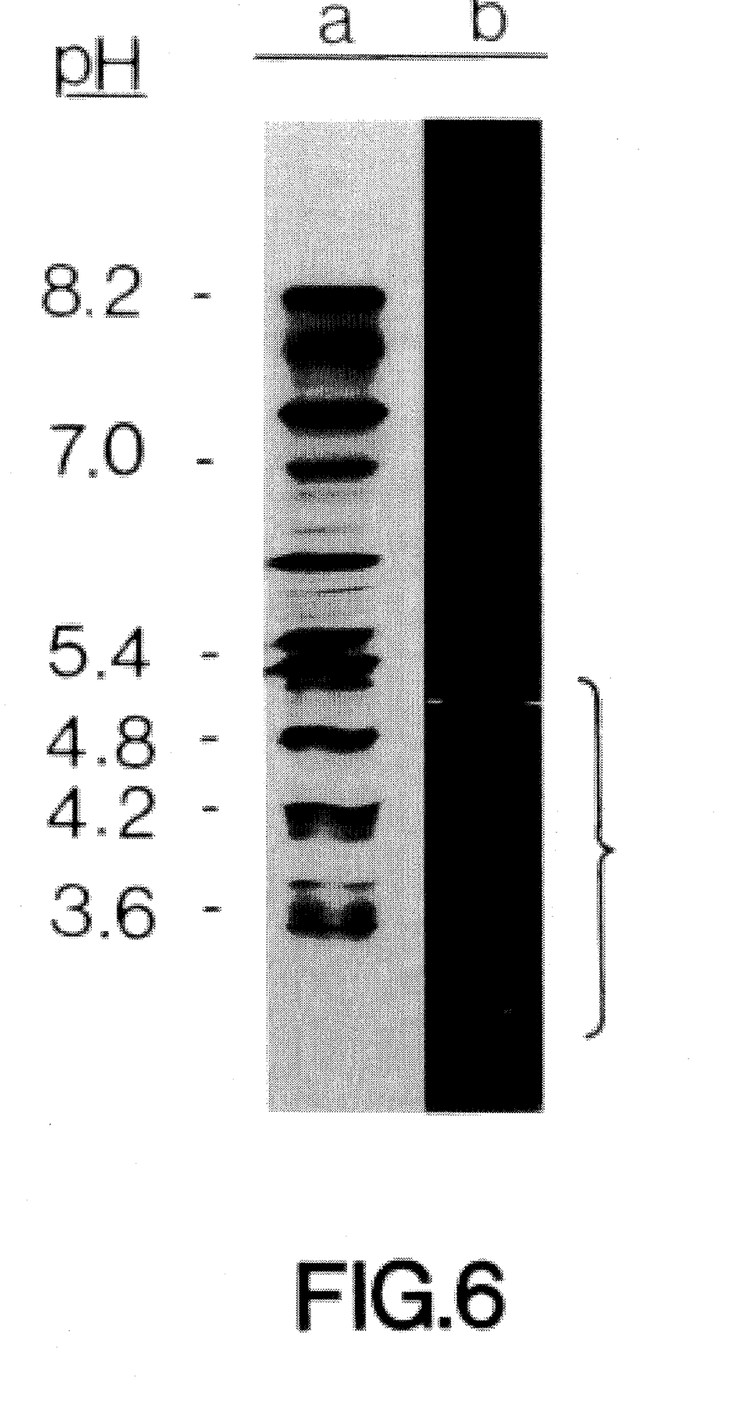
FIG. 6 is a photograph of results of isoelectric focusing of a gel containing affinity-purified GSA 65. Lane a contains Coomassie blue-stained protein standards; lane b contains trichloroacetic acid precipitate of GSA 65 as photographed in a light diffraction box. Bracket indicates the acidic pH region in which GSA 65 smeared.

As seen in FIG. 6, agarose isoelectric focusing gels, GSA 65 migrated with the low pH standards but failed to resolve into a single well-focused band. Instead, GSA 65 smeared broadly from pH 5.4 to a region far below that of the protein standard with the lowest pI (amylglycosidase [pI 3.6]). The most intense banding was seen below pH 4, indicating that GSA 65 is very acidic. This smearing was reproducible from run to run. All pH standards were well resolved and stained intensely with Coomassie blue R-250.

GSA 65 resistance to proteolytic degradation and boiling. Its sensitivity to periodic acid oxidation suggest that this antigen contains carbohydrate. GSA 65 behaves as a glycoprotein in that it is highly water soluble, precipitates in ammonium sulfate and trichloroacetic acid, and stains intensely with periodic acid-Schiff reagent in polyacrylamide gels. SDS-PAGE and IEF banding patterns confirmed that GSA 65 is a glycoprotein. Because of differential glycosidation, glycoproteins have a variable charge-to-mass ratio and hence often fail to resolve into single bands characteristic of a pure protein by most electrophoretic techniques. Sharon, N., *Complex Carbohydrates,* Addison-Wesley, Reading, Mass. (1975). GSA 65 gave a characteristic glycoprotein fingerprint in Western blots and in agarose IEF gels.

Carbohydrate and protein assays suggested that GSA 65 is highly glycosylated. GSA 65 has approximately a 1:4 carbohydrate/protein mass ratio, which translates to roughly 1 hexose monosaccharide per 9 to 10 amino acids. This is comparable to the glycosylation ratio found in many mucins.

EXAMPLE 5

Stability of GSA 65 Under Storage Conditions

*G. lamblia* cyst-positive stool eluates that were previously verified GSA 65 positive by CIE were resistant to Formalin fixation and prolonged storage. Formalin-fixed and untreated GSA 65-positive stools gave characteristic precipitin arcs in CIE after storage for 6 months at 4 or −20° C. No precipitin arcs were observed in negative controls.

EXAMPLE 6

Coprodiagnostic Assay for GSA 65

GSA 65 was detected in aqueous extracts of human fecal specimens as follows. Stool specimens (100 ul) were diluted (1:20 v/v) in a specimen dilution buffer comprising tris buffer with surfactant and preservatives (available commercially as Specimen Dilution Buffer from Alexon Biomedical, Inc., Mountain View, Calif.) to create a stool eluate. Stool eluate (200 ul) was added to immunoassay tubes, preferably polystyrene, precoated with monospecific anti-GSA 65 antibody. The precoated tubes are available commercially as Precoated Star Tubes® from Alexon Biomedical, Inc., Mountain View, Calif. (Star Tube is a registered trademark of Nunc, Inc.). The contents of the tube are then incubated at about 20°–25° C., preferably 22° C., for one hour. Other solid phase substrates, for example, membranes, may also be used to carry out the assay method.

After incubation, unbound material was washed from the tube with three 3 ml washes of diluted immunoassay wash buffer comprising 10x concentrated phosphate buffer with detergent (available commercially as Immunoassay Wash Buffer from Alexon Biomedical, Inc., Mountain View, Calif.). Anti-GSA 65 linked to the enzyme horseradish peroxidase diluted in phosphate buffer with fetal calf serum and preservative (200 ul) (available commercially as Enzyme-Antibody Conjugate from Alexon Biomedical, Inc., Mountain View, Calif.) was added to the tube. The contents were then incubated for one hour at about 20°–25° C., preferably 22° C. Excess unbound anti-GSA 65-HRP material was washed from the tube and decanted from the tube using four 3 ml washes using the above-described immunoassay wash buffer.

Following the last wash, the tube is left inverted for 2–3 minutes. An O-phenylenediamine (OPD)/peroxide enzyme substrate solution (200 ul) made from Peroxide Buffer (citrate phosphate buffer with hydrogen peroxide) and OPD Tablets, (1 tablet in 4 ml buffer) both commercially available from Alexon Biomedical, Inc., Mountain View, Calif., was added to the tube and incubated for 10 minutes at 20°–25° C., preferably 22° C. As a final step, 50 ul of dilute acid solution (2N sulfuric acid) (available commercially as Dilute Acid Solution from Alexon Biomedical, Inc., Mountain View, Calif.) was added to stop the reaction.

The enzyme of the bound anti-GSA 65-HRP, which depends on the presence of the GSA 65 antigen in the fecal sample, reacts with the substrate to produce a yellow color which is visually detected. Distinct yellow or yellow-brown reactions indicate presence of GSA 65 in the stool specimen; color intensity is proportional to the concentration of GSA 65 in the stool. Negative reactions do not develop color.

Initially the sensitivity of the immunoassay was tested using 93 *Giardia lamblia* O&P-positive clinical specimens collected at the Holy Family and Sacred Heart Hospitals from July of 1986 to August of 1987. All 93 of these specimens were strongly positive by visual examination using the immunoassay. Of these specimens, 87 had optical densities (O.D.s) greater than 2.00 (off-scale on the Dynatec™ MR 580 spectrophotometer) and the remaining six had O.D.s greater than 1.00. (The eye can easily detect down to 0.40 O.D. in the yellow range.) The average O.D. of the 93 specimens was 1.95. There was no correlation between the quantity of cysts or trophozoites present in stool specimens by microscopic examination or stool consistency and the final optical density generated by the test as seen in Table 3. Four negative control stool specimens (two of which were run in duplicate) were visually devoid of color following assay. Their respective O.D.s were 0.168, 0.164, 0.163, 0.183, 0.149 and 0.158.

TABLE 3

Quantities of Giardia cysts and/or trophozoites found in stool specimens, and immunoassay outcome O.D.s in the Spokane and San Francisco study populations. In both populations there was a poor correlation between the number of parasites observed by O&P examination and immunoassay O.D. generation.

| | Spokane Specimens | | San Francisco Specimens | |
|---|---|---|---|---|
| Quantity of Giardia on O&P examination: | Number Specimens: | Average Immunoassay O.D.: | Number Specimens: | Average Immunoassay O.D.: |
| None | 1 | 2.000 | 6 | 1.608 |
| Rare | 2 | 2.000 | 4 | 0.525 |
| Occasional | n/a† | n/a† | 1 | 1.234 |
| Few | 25 | 2.000 | 4 | 1.300 |
| Moderate | 40 | 1.930 | 5 | 1.698 |
| Many (Abundant) | 25 | 1.922 | 3 | 1.500 |

†Spokane facilities did not use "occasional" in their parasite count protocol.

TABLE 3-continued

Quantities of Giardia cysts and/or trophozoites found in stool specimens, and immunoassay outcome O.D.s in the Spokane and San Francisco study populations. In both populations there was a poor correlation between the number of parasites observed by O&P examination and immunoassay O.D. generation.

| | Spokane Specimens | | San Francisco Specimens | |
|---|---|---|---|---|
| Quantity of Giardia on O&P examination: | Number Specimens: | Average Immunoassay O.D.: | Number Specimens: | Average Immunoassay O.D.: |

Rare = 1–5 per 22 mm coverslip.
Occasional = 6–10 per 22 mm coverslip.
Few = 11–20 per 22 mm coverslip.
Moderate = 21–40 per 22 mm coverslip.
Many (Abundant) = >40 per 22 mm coverslip.

These satisfactory results led to development of a clinical trial at the Refugee Screening Clinic. From August to October of 1987, 208 patient stool specimens were collected. Of these specimens, 16 were positive by O&P examination and by immunoassay, 6 were negative by O&P examination and positive by immunoassay, and 1 was positive by O&P examination and negative by immunoassay. The average optical density of the 22 specimens judged visually positive was 1.36. Eight had O.D.s greater than 2.00, ten had O.D.s greater than 1.00, and the remaining four had O.D.s ranging from 0.474 to 0.659. The mean optical density and standard deviation of the 186 specimens judged as visually negative was 0.180 (±0.04). Similar to the Spokane study specimens, there was a poor correlation between the microscopically observed cyst or trophozoite count and the intensity of immunoassay color development. The results are shown in Table 3.

In addition, 51 stool specimens containing 15 intestinal parasites other than Giardia by O&P examination were collected at San Francisco General Hospital from August to October of 1987. These specimens were used for cross-reactivity testing of the immunoassay as seen in Table 4. Twenty-seven of these specimens were collected from the Refugee Screening Clinic; the remaining 24 were collected from patients seen at other clinics. Of the 51 specimens collected, only 2 positive reactions were observed. The assay optical densities of these two specimens were 1.128 and 1.157, respectively. The optical density mean and standard deviation of the remaining 49 negative specimens were 0.181 (±0.036).

TABLE 4

A compiled list of all parasites, other than *Giardia lamblia*, represented in the cross-reactivity test panel.

| Intestinal Parasite | Specimens with parasite | Number of Positive Reactions Out of All Specimens Tested in Each Category |
|---|---|---|
| *Ascaris lumbricoides* | 9 | 1/9 |
| *Blastocystis hominis* | 3 | 0/3 |
| *Chilomastix mesnili* | 2 | 0/2 |
| *Clonorchis sinensis* | 1 | 0/1 |
| Cryptosporidium | 4 | 0/4 |
| *Entamoeba coli* | 9 | 1/9 |
| *Entamoeba hartmanni* | 2 | 0/2 |
| *Entamoeba histolytica* | 3 | 0/3 |
| *Endolimax nana* | 8 | 0/8 |
| Hookworm | 8 | 0/8 |
| *Hymenolepis nana* | 2 | 0/2 |

TABLE 4-continued

A compiled list of all parasites, other than *Giardia lamblia*, represented in the cross-reactivity test panel.

| Intestinal Parasite | Specimens with parasite | Number of Positive Reactions Out of All Specimens Tested in Each Category |
|---|---|---|
| *Iodamoeba buetschlii* | 6 | 0/6 |
| *Isospora belli* | 1 | 0/1 |
| *Strongyloides stercoralis* | 1 | 0/1 |
| *Trichuris trichuria* | 8 | 0/8 |

As indicated in Table 4, positive reactions were recorded in only two cases. These reactions most likely represent cryptic cases of giardiasis rather than true cross-reactions, due to the lack of reactivity with several other specimens in each category containing the same parasite. Both of these individuals came from families having members with concurrent giardial infection.

The ability of the Specimen Dilution Buffer to stabilize several common stool fixatives and a stool transport medium was used to determine these agents' compatibilities with the immunoassay. Each agent was considered compatible if its post-dilution pH was ≧7.0. At this pH, antigen-antibody interactions critical to the outcome of the diagnostic test occur at an acceptable rate. SAF fixative, 10% Formalin, and Cary-Blair medium had post-dilution pHs of 7.0–7.5 and were compatible with the immunoassay. PVA was incompatible with the immunoassay because its post-dilution pH was low (6.0–6.5).

All 30 of the treated Giardia O&P-positive stool specimens were clearly positive by immunoassay in all treatment categories. Treatment of stools with any of the above-listed agents did not significantly alter the immunoassay sensitivity. Spectrophotometrically, a small loss in optical density generation was observed between identical stools treated with the listed agents. Agents giving the best performance were the PBS-T control and Cary-Blair Medium, followed closely by SAF fixative and 10% Formalin. The respective O.D. mean and standard deviation (mean ±S.D.) of the 30 specimens in each agent treatment category were as follows: PBS-T (1.730± 0.449); Cary-Blair medium (1.667±0.478); SAF fixative (1.658±0.497); and 10% Formalin (1.556±0.495). The six negative controls did not develop observable color and had an average optical density of 0.164. There was negligible loss in assay sensitivity when specimens were treated with Cary-Blair transport medium, SAF fixative, or 10% Formalin. Positivity was visually detected at specimen dilutions in excess of 1:1,000 in all treatment categories.

What is claimed is:

1. A method for the coprodiagnosis of giardiasis in mammals comprising:

(a) incubating an eluate of a stool specimen obtained from a mammal, with a solid support precoated with a first composition consisting essentially of antibodies monospecific to *Giardia lamblia*-specific antigen (GSA 65) wherein any GSA 65 antigen present in the eluate binds to said precoated solid support;

(b) washing unbound components of the eluate from the solid support;

(c) incubating a second composition consisting essentially of antibodies monospecific to GSA 65 with said solid support wherein said second composition is bound to any GSA 65 antigen bound to the solid support;

(d) washing unbound components of the second composition from the solid support; and (e) detecting antibodies from said second composition bound to solid support.

2. The method of claim 1 wherein the antibodies of said second composition are conjugated to an enzyme.

3. The method of claim 2 wherein said detecting includes, after step (d), incubating color-forming substrate for said enzyme with said solid support; and observing color formation.

4. The method of claim 3 wherein said observing is conducted visually without instrumentation.

5. The method of claim 1 which further includes conduct of a negative control which comprises the steps of:

(a) incubating an negative control with a solid support precoated with a first composition consisting essentially of antibodies monospecific to *Giardia lamblia*-specific antigen (GSA 65);

(b) washing unbound components of the negative control from the solid support;

(c) incubating a second composition consisting essentially of antibodies monospecific to GSA 65 with said solid support, (d) washing unbound components of the second composition from the solid support; and (e) detecting the absence of bound antibodies from said second composition.

6. The method of claim 5 wherein the antibodies of said second composition are conjugated to an enzyme.

7. The method of claim 6 wherein said detecting includes, after step (d), incubating color-forming substrate for said enzyme with said solid support; and observing absence of color formation.

8. The method of claim 6 wherein said observing is conducted visually without instrumentation.

9. The method of claim 2 wherein said enzyme is peroxidase.

10. The method of claim 6 wherein said enzyme is peroxidase.

* * * * *